United States Patent [19]

Andary et al.

[11] Patent Number: 5,719,129
[45] Date of Patent: Feb. 17, 1998

[54] DERIVATIVE OF CAFFEIC ACID, ORAPOSIDE, AND COSMETIC OR PHARMACEUTICAL COMPOSITIONS, IN PARTICULAR DERMATOLOGICAL COMPOSITIONS, CONTAINING IT

[75] Inventors: Claude Andary, Montpellier Cedex; Patrice Andre, Neuvilles aux Bois, both of France

[73] Assignee: Parfums Christian Dior, Paris, France

[21] Appl. No.: 119,172

[22] PCT Filed: Mar. 21, 1991

[86] PCT No.: PCT/FR91/00229

§ 371 Date: Oct. 15, 1993

§ 102(e) Date: Oct. 15, 1993

[87] PCT Pub. No.: WO92/16544

PCT Pub. Date: Oct. 1, 1992

[51] Int. Cl.$^6$ .................... A61K 31/70; C07M 15/00
[52] U.S. Cl. .................. 514/25; 536/4.1; 536/18.1
[58] Field of Search .................... 536/4.1, 18.1; 514/25

[56] References Cited

FOREIGN PATENT DOCUMENTS

| 2302745 | 3/1975 | France . |
| 2314725 | 3/1975 | France . |
| 2652086 | 9/1989 | France . |

OTHER PUBLICATIONS

Chemical Abstracts, vol. 106, No. 19, May 11, 1987, p. 574, Abstract 155103s.
Chemical Abstracts, vol. 107, No. 6, Aug. 10, 1987, p. 407, Abstract 46141c.
Chemical Abstracts, vol. 107, No. 7, Aug. 17, 1987, p. 37, Abstract 51592e.
Chemical Abstracts, vol. 114, No. 10, Mar. 11, 1991, p. 423, Abstract 88423w.

*Primary Examiner*—Elli Peselev
*Attorney, Agent, or Firm*—Foley & Lardner

[57] ABSTRACT

The invention relates to a new derivative of caffeic acid.

This new derivative has the formula I below:

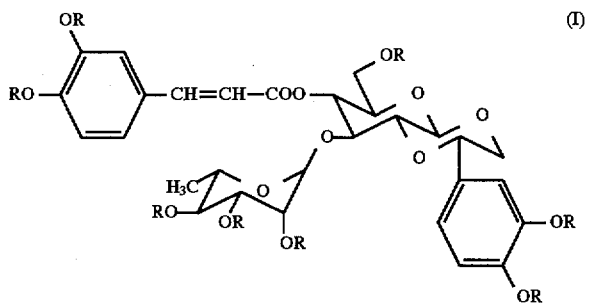

in which one or more R independently represent a hydrogen atom, a $C_1$–$C_5$ alkyl group, in particular methyl, and an acyl group, in particular a $C_1$–$C_6$ group, in particular acetyl.

This new derivative called oraposide is particularly useful for the preparation of cosmetic or pharmaceutical compositions, in particular dermatological compositions, as a result in particular of its activity against free radicals, inflammation and aging due to radiation exposure.

26 Claims, 2 Drawing Sheets

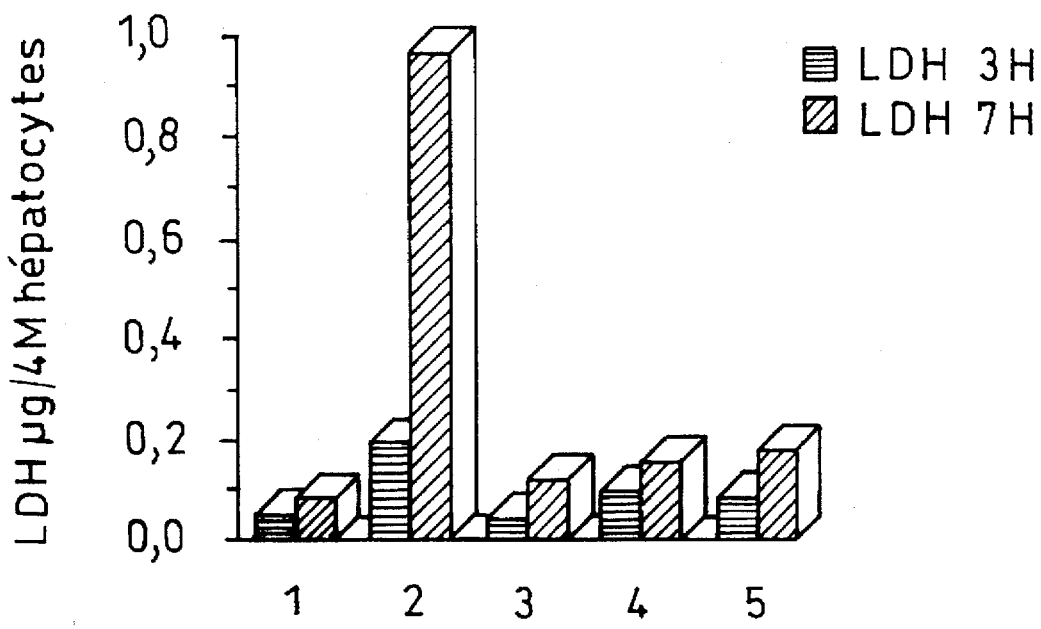
fig_1
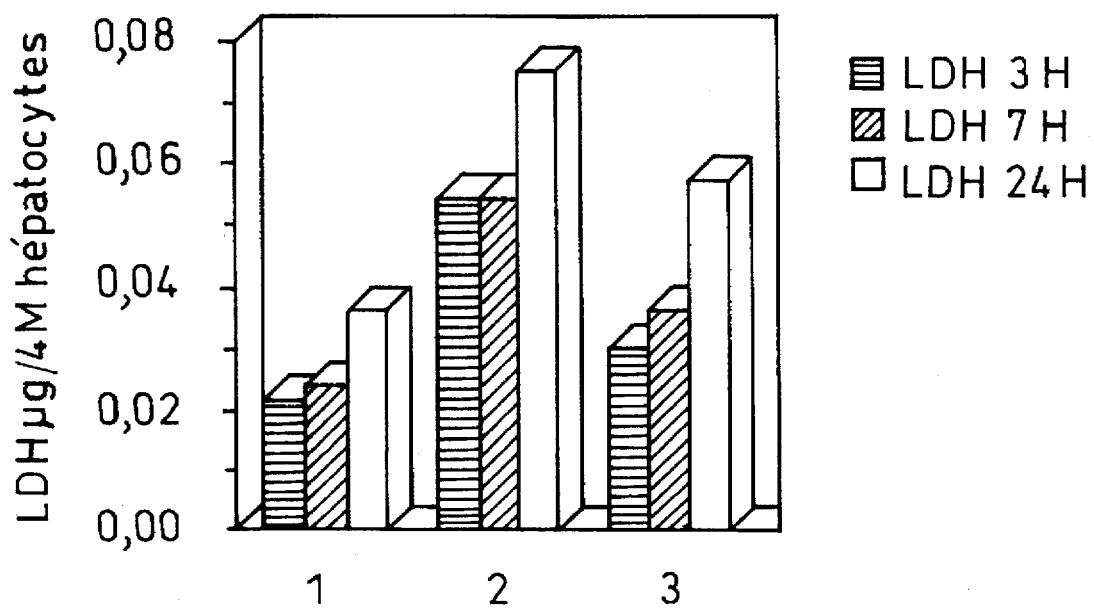
fig_2

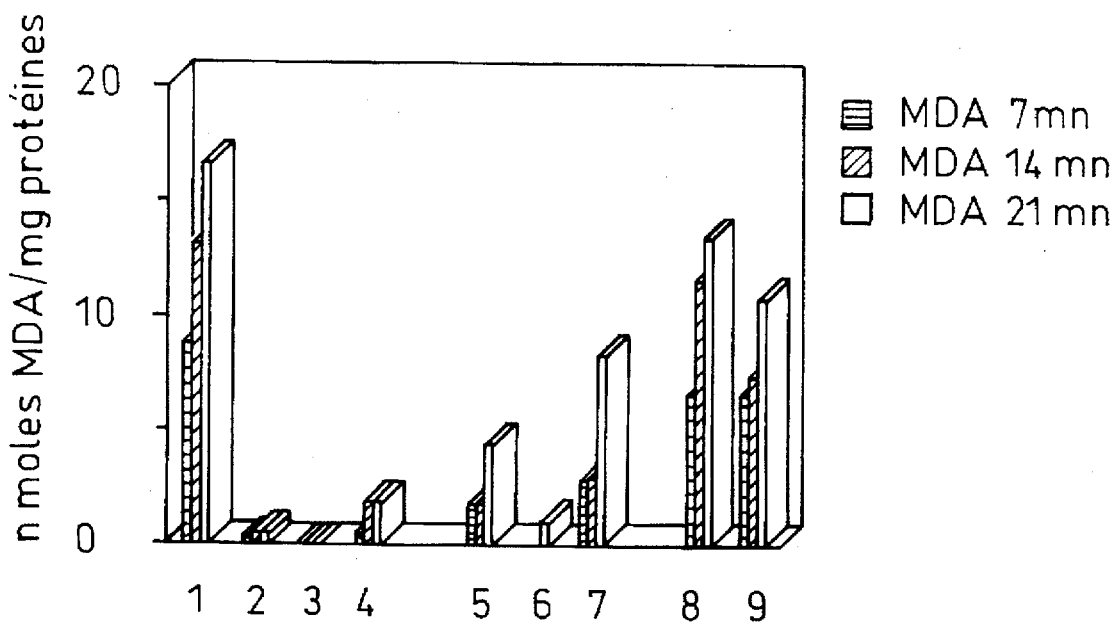
fig_3
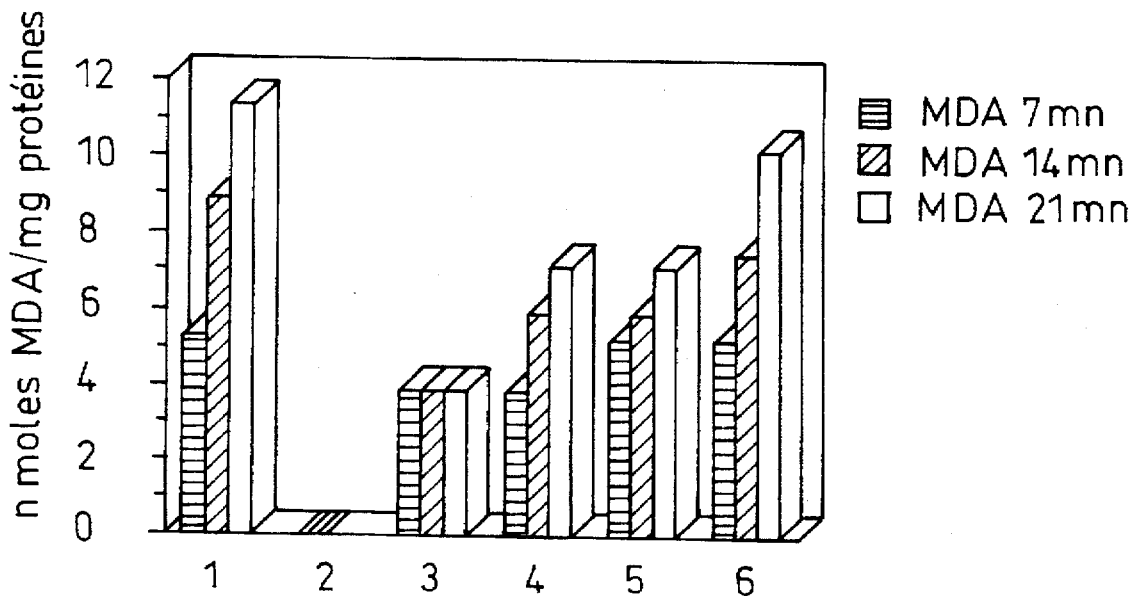
fig_4

DERIVATIVE OF CAFFEIC ACID, ORAPOSIDE, AND COSMETIC OR PHARMACEUTICAL COMPOSITIONS, IN PARTICULAR DERMATOLOGICAL COMPOSITIONS, CONTAINING IT

This invention relates essentially to a new derivative of caffeic acid, oraposide, and cosmetic or pharmaceutical compositions, in particular dermatological compositions, containing it.

More particularly, the new derivative according to the invention, oraposide, is a derivative of caffeic acid extracted from plants of the Orobanchaceae family. The invention also relates to particular derivatives of oraposide, in particular acylated derivatives, and plant extracts containing it, in particular extracts from the broomrape, *Rapum genistae*.

Preliminary investigations had already revealed that caffeic acid derivatives are present in extracts from the Orobanchaceae, parasitic phanerogamic plants which do not contain chlorophyll (Andary et al., 1980, Il Farmaco, 1, 1–30; Bridel and Charaux, 1924, C.R. Acad. Sci. 178, 1839), but their structure had not been clearly established.

The pharmacological benefits of caffeic acid (or 3,4-dihydroxycinnamic acid) and several natural derivatives of it have already been the object of many investigations. Thus Kimura et al. (Planta Medica, 1984, 473–477) have investigated the effect of various tannins and in particular caffeic acid and caffeoylquinic acid derivatives extracted from plants of the species Artemisia and have demonstrated their inhibitory effect on the peroxidation of lipids in rat liver mitochondria and microsomes. The inhibitive effect of these molecules on the lipoxygenases which are involved in leucotriene and arachidonic acid metabolism and their potential use in the treatment of inflammatory conditions like asthma have also been published by Kimura and Okuda (J. of Natural Products, 1987, 50, 392–399).

As different caffeic derivatives are active in a variety of ways which vary in relation to their structure, it is of advantage to investigate new molecules in this family, in medicinal or other plants, and to search for new pharmacological activities or improved performance.

Thus a new compound, which has particularly interesting properties, has been obtained from extracts of plants of the Orobanchaceae family which parasitise various brooms (*Cytisus scoparius* and *purgans*) as well as food plants such as lentils, beans and the Solanaceae (tomatoes, aubergines). The broomrape is a perennial plant comprising a stem with a flowering spike, and the whole plant may attain a length of 20 to 100 cm, with scales all along the stem, which ends at the base in a bulb which is also covered with scales. The entire plant is rich in heteroside caffeic ester derivatives. The bulb, the organ which is attached to the roots of the host plant by tendrils in the form of small roots, is the organ containing the highest concentrations of these heteroside caffeic esters.

The substance extracted from the broomrape, *Rapum genistae*, has been obtained in a pure crystallised form, e.g. by steeping an extract of the plant or plant cells in alcohol, and has been subjected to various conventional analyses which have made it possible to establish its molecular configuration and structure (chromatographic separations, determination of melting point, investigation of NMR spectra, mass spectra, X-ray, IR and UV spectra and various biochemical analyses). The formula which has been deduced from these analyses is as follows: 3-0-(α-L-rhamnopyranosyl)-[2-(3,4-dihydroxyphenyl)-1,2-ethylidene]-β-D-glucopyranoside 4-caffeate.

This substance, which it has been proposed should be called "oraposide", is represented by a formula (I) below, in which R is a hydrogen atom.

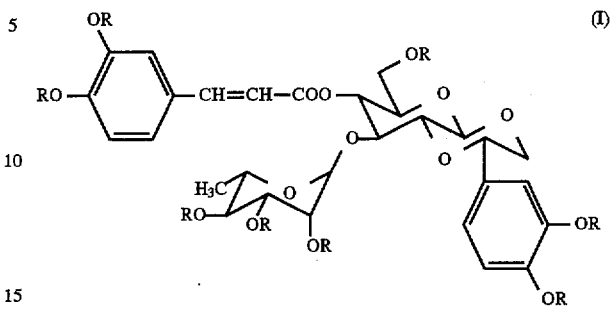

This invention also relates to derivatives of formula I in which one or more R independently represent an atom of hydrogen, a lower $C_1$–$C_5$ alkyl, in particular methyl, or an acyl group, in particular one containing $C_1$–$C_6$, in particular acetyl.

In accordance with another preferred feature, only the OR groups on the benzene rings are alkylated, and in particular methylated.

Preferably, only the OR groups on glucopyranosyl or rhamnopyranosyl rings are acylated, in particular acetylated.

In particular, oraposide or its derivatives are extracted from a plant of the Orobanchaceae family, in particular the broomrape, *Rapum genistae*.

Derivatives of this kind can be obtained by conventional methods which are well known to those skilled in the art.

In particular, to prepare the peracetylated derivatives of oraposide, a simple method may be used which consists of dissolving crystals of oraposide in one volume of acetic anhydride to which one volume of pyridine is added. This is allowed to stand overnight at ambient temperature. The next day it is filtered, and the derivative according to the invention is redissolved and freeze dried. This yields the peracetylated derivative of oraposide, i.e. all the OR groups on the glucopyranosyl or rhamnopyranosyl rings are acetylated.

It has now been discovered, unexpectedly, that oraposide and its aforementioned derivatives have many chemical and biochemical effects such as trapping free radicals, antioxidant effects, preventing in particular the peroxidation of lipids, aldose reductase inhibition, 5-lipoxygenase inhibition, dopa-decarboxylase inhibition, adrenergic β-blocking, anti-tremor effects, anti-allergenic effects, and analgesic, bactericidal and fungicidal effects, and have a wide absorption band for ultraviolet UVA and UVB radiation, which enables them to be used advantageously as a solar filter.

Thus, oraposide, its aforesaid derivatives, and plant extracts containing it are particularly valuable, especially in the fields of pharmaceuticals, cosmetics and foodstuffs.

In accordance with a second feature, this invention also relates to a cosmetic or pharmaceutical composition, in particular a dermatological composition, characterised in that it comprises, as the active ingredient, oraposide or its derivatives of formula I as defined above, in which one or more R independently represent an atom of hydrogen, a lower $C_1$–$C_5$ alkyl, in particular methyl, or an acyl group, in particular a $C_1$–$C_6$ group, in particular acetyl, or a plant extract containing it. Preferably the acylated derivatives are such that only the OR groups on the glucopyranosyl or rhamnopyranosyl rings are acylated, in particular acetylated. Again preferably the alkylated derivatives are such that only the OR groups on the benzene rings are alkylated, in particular methylated.

In accordance with an advantageous embodiment, oraposide or its aforesaid derivatives are incorporated in a final composition in a proportion lying between approximately 0.001 and approximately 10% by weight, preferably between 0.1 and 5% by weight.

In accordance with a particular embodiment, the composition according to the invention is a composition which has the effect of trapping free radicals, inhibiting aldose reductase, inhibiting 5-lipoxygenase, inhibiting dopadecarboxylase, acting as a β-blocker, preventing tremor or filtering ultraviolet UVA and UVB radiation.

In accordance with an advantageous variant the compositions according to the invention as defined above contain no additional antibacterial or antifungal preservative, nor any additional antioxidant; in particular against the oxidation of the lipids in the cosmetic or pharmaceutical composition.

The formulation will of course be adapted in relation to its desired purpose. The composition may therefore be formulated in the form of an injectable dose, or for oral administration or for external treatment by topical application. The excipient will therefore be appropriate to this formulation and will be a cosmetically or pharmaceutically acceptable excipient.

The compositions according to the invention are particularly effective in preventing aging of the skin and in the treatment of inflammatory conditions frequently accompanying solar erythema. In fact in some metabolic conditions or disturbances having an external origin, such as exposure to ultraviolet radiation, oxygen reduction is incomplete and results in the formation of free radicals which can cause deterioration of the phospholipids in cell membranes. The production of free radicals gives rise to various physiopathological conditions which contribute to cell aging and probably to carcinogenesis, inflammatory phenomena and the process of liver intoxication.

Thus compositions according to the invention are intended in particular to treat inflammations, both by local application and by systemic means, in particular inflammations caused by excessive exposure to the sun, to control cell aging, in particular against radiation-induced aging of the skin, and to protect the skin against ultraviolet UVA and UVB radiation, and to prevent and treat pigmented marks on the skin. They are also effective in the treatment of liver intoxication, regardless of its origin, and in the treatment of diabetes, in particular diabetes mellitus, and the disturbances in the lens which are frequently associated with it, and as an analgesic, antiallergic, psychotropic, antiparkinsonian and antihypertensive agent.

In accordance with a particular embodiment of the invention within the context of antitremor treatment, in particular in Parkinson's disease, the composition according to the aforesaid invention also contains a therapeutically effective amount of L-dopa. In fat oraposide and its derivatives of formula I aforesaid have a potentiating activity for L-dopa in its antitremor activity, which is effective in particular in Parkinson's disease. Oraposide and its derivatives of formula I aforesaid associated with L-dopa in fact experimentally reduce tremor caused by a tremor-inducing factor in animals and in man. In Parkinson's disease an improvement in abnormal movements (of the choreic type) and other secondary disturbances due to treatment with L-dopa is found.

The invention will now be described in detail with reference to several example embodiments which are provided merely by way of illustration and which therefore do not restrict the scope of the invention. These examples are also given with reference to a number of figures, included in the appended drawings, in which:

FIG. 1 shows the amount of LDH (lactate dehydrogenase) released by $4.10^6$ hepatocytes (8 day culture) into the culture medium 3 and 7 hours after treatment. Reference 1 in the two blocks of histograms indicates the results obtained with untreated cultures, acting as controls, reference 2 indicates histogram blocks obtained using cultures treated with nitroxynil at a concentration of $10^{-4}$M, reference 3 indicates histogram blocks obtained with cultures treated with nitroxynil in a concentration of $10^{-4}$M and verbascoside in a concentration of $5.10^{-5}$M, reference 4 indicates histogram blocks obtained with cultures treated with nitroxynil in a concentration of $10^{-4}$M and oraposide in a concentration of $5.10^{-5}$M, and reference 5 indicates histogram blocks obtained with cultures treated with nitroxynil in a concentration of $10^{-4}$M and arenarioside in a concentration of $5.10^{-5}$M. Nitroxynil is a hepatotoxic agent, verbascoside and arenarioside are other heteroside esters of caffeic acid which are known to those skilled in the art.

FIG. 2 shows the amount of LDH (lactate dehydrogenase) released by $4.10^6$ hepatocytes (24 hour culture) into the culture medium 3, 7 and 24 hours after treatment. As in FIG. 1, reference 1 indicates the results obtained with untreated cultures, reference 2 the results obtained with cultures treated with $10^{-4}$M chloroform, and reference 3 the results obtained with cultures treated with a combination of $10^{-4}$M chloroform and oraposide in a concentration of $5.10^{-5}$M. Chloroform is also a hepatotoxic agent.

FIG. 3 shows the inhibition of lipoperoxidation on liver microsomes by different phenolic compounds at $5.10^{-5}$M in the reaction medium. Reference 1 indicates histogram blocks obtained with the control lot without phenolic compound, reference 2 indicates the results obtained with verbascoside, reference 3 indicates the results obtained with oraposide, reference 4 indicates the results obtained with arenarioside, reference 5 indicates the results obtained with rosmarinic acid, reference 6 indicates the results obtained with isochlorogenic acid, reference 7 indicates the results obtained with chicoric acid, reference 8 indicates the results obtained with caffeic acid and reference 9 indicates the results obtained with vitamin E (α-tocopherol). Verbascoside, oraposide and arenarioside are heteroside esters of caffeic acid and the acids cited are other esters of caffeic acid.

FIG. 4 indicates the inhibition of lipoperoxidation by oraposide at different concentrations on liver microsomes in rabbits. Reference 1 indicates the results obtained with the reference lot without oraposide, reference 2 the results obtained with oraposide in a concentration of $5.10^{-5}$M, reference 5 the results obtained with oraposide in a concentration of $5.10^{-6}$M, reference 4 the results obtained with oraposide in a concentration of $5.10^{-6}$M, reference 5 the results obtained with oraposide in a concentration of $2.10^{-6}$M and reference 6 the results obtained with oraposide in a concentration of $10^{-6}$M.

EXAMPLE 1

Preparation of the Plant Extract, Purification of the Crystals, Analysis and Establishment of the Formula of Oraposide The starting material is powdered plant (broomrape) defatted with petroleum ether. This powder is steeped in 80% ethanol or 80% methanol in the proportion of 10 l per 400 g of plant powder at 50° C. the extract obtained is concentrated and freeze dried. This freeze dried extract, called "crude broomrape extract" contains 3 to 5% by weight of oraposide.

After filtration, 20 ml of a freshly prepared aqueous solution of 10% sodium metabisulphite is added quickly to this alcoholic residue. After standing overnight at 4° C. the extract is filtered and then concentrated in such a way as to eliminate the alcohol. The extract, which is now aqueous, is subjected to final defatting using a mixture of peroxide-free ethyl ether—petroleum ether (3:1). This defatted extract is repeatedly extracted with 20 l of ethyl acetate (redistilled over calcium chloride). The "ethyl acetate" phases are dried using sodium sulphate (pure, dry), then combined and evaporated to dryness under vacuum. The powdery residue obtained, which is creamy white in colour, called "purified broomrape extract", contains approximately 30% by weight of oraposide. This purified extract can be dissolved in hot water and the solution can be crystallised at ambient temperature and then at +4° C. in order to perform a further purification.

These crystals are dried and redissoived hot in a mixture of 5% ethanol—95% water and then recrystallised cold. This operation is repeated several times.

The component obtained in the pure crystalline state was subjected to various conventional biochemical and physical and chemical analyses. Its rotation power was determined to be $(\beta)^{22D} = -110.3°$ (methanol). The melting point was 210° C. The NMR $^1H$ spectrum ($\delta$ in PPM) was:

7.46 and 6.18 (2H,2xd, J=16 Hz, trans R—CH═CH—R bond),

5(1H,d,J=1 Hz, H–1 Rha), 4.92(1H,t J=9,5 Hz, H–3 Glc), 4.57(1H,tJ=2,5,9 Hz, H–7' Aglycone), 4.55(1h,d,J=7,8 Hz, H–1 Glc), 4.05(1H,t J=9,5 Hz, H–3 Glc), 3.94–3.71(2H,m,J=12 Hz, 2H–6 Glc), 3.57(1H,dd,J=1,3 Hz, H–2' Rha), 3.45(1H,m,H–8' Aglycone), 3.38(1H,dd,J=7,8,9,5 Hz, H–2 Glc), 1.05(3H,dJ=6 Hz, 3H–1 Rha).

The UV spectrum obtained using equipment of the Kontron Uvikon 860® type showed a UVA absorption maximum at 330 nm and a UVB peak at 290 nm. Integration of the surface areas of the UVB peaks can be used to compare oraposide with Parsol MCX®, from which it can be seen that the UVB absorption activity of oraposide is 0.4 times that of Parsol MCX®. If the surface area of the UVA peak of oraposide is integrated and compared with Parsol 1 789®, it will be seen that the UVA absorption of oraposide is approximately 0.2 times that of Parsol 1 789®. Investigation of the above results and the mass spectra and X and IR spectra can be used to demonstrate that oraposide is a 4-caffeate of 3-0-(α-L-rhamnopyranosyl)-[2-(3,4-dihydroxyphenyl)-1,2-ethylidene]-β-D-glucopyranoside.

EXAMPLE 2

In Vitro Investigation of the Properties of Oraposide in the Protection of Rabbit Hepatocytes in Culture The experimental model selected was investigation of the release of lactate dehydrogenase (LDH) by rabbit hepatocytes in primary culture, this LDH release representing a marker of hepatocyte deterioration.

The hepatocytes were deliberately intoxicated with nitroxynil ($10^{-4}$ to $10^{-5}M$) or chloroform ($10^{-3}$ to $10^{-5}M$).

The effect of oraposide was evaluated for a final concentration of 0.05 mM in the culture medium.

FIG. 1 shows that oraposide very significantly reduces the release of LDH by hepatocytes intoxicated with nitroxynil and FIG. 2 shows a less clear effect on cells treated with chloroform, but this has a less toxic effect.

Oraposide itself has no cell toxicity, even at a concentration of 100 µM.

EXAMPLE 3

In Vitro Investigation of Lipoperoxidation Inhibition in Rabbit Liver Microsomes A lipoperoxidation reaction takes place when rabbit liver microsomes are incubated in the presence of NADPH.

The microsomes were recovered from the processing of hepatocytes with ultrasound.

Lipoperoxidation was evaluated through the formation of malonyl dialdehyde in accordance with the method by Placer et al., 1966 (Analyt. Biochem. 16,359–364).

The reaction was performed in the absence of (control) and in the presence of caffeic acid or oraposide in a concentration of $5.10^{-5}M$ or in the presence of α-tocopherol (Sigma) at $5.10^{-5}M$ (known inhibiting activity reference).

FIG. 3 clearly shows that caffeic acid and α-tocopherol have equivalent inhibiting activity and that oraposide shows stronger inhibition (100%).

The dose of oraposide required to obtain 50% inhibition is $10^{-5}M$ (FIG. 4).

Furthermore the oxidation of membrane lipids by free radical generators ($CCl_4$ and $H_2O_2$) can be potentiated. Under these conditions inhibition by oraposide is 100% with $CCl_4$ and 90% with $H_2O_2$.

EXAMPLE 4

Detection of an Antibacterial and Antifungal Effect

It is known that a number of caffeic acid derivatives inhibit the growth of bacteria and fungi. This property has been confirmed for oraposide with 40 different strains belonging to 10 genera of bacteria, and 25 different strains belonging to 25 species of fungi.

100% inhibition of all bacterial strains was observed with doses of 0.5 mg/ml and above. The bacterial strains tested were: *Staphylococcus aureus*, Streptococcus (group A and group D), *Escherichia coli*, *Klebsiella pneumoniae*, *Proteus sp.*, *Providentia sp.*, *Serratia marcescens*, *Enterobacter cloacae*, *Pseudomonas aeruginosa*, Salmonella (*S. typhi* and *S. para-typhi*).

A more detailed investigation performed using 29 strains of the bacterium *Staphylococcus aureus* showed 70% inhibition at a concentration of 0.06 mg/ml and 80% at 0.12 mg/ml.

Antifungal activity was tested in relation to micromycete contaminants commonly found in foodstuffs. The test was performed with 25 species belonging to the Adelomycetes (e.g. *Alternaria tenuis*, *Fusarium avenceum*, *Geotricom candidum*, etc.), Mucorales (e.g. *Mucor mucedo*, *Cunninghamella elegans*, *Rhizopus nigricans*, etc.), Endomycetes (e.g. *Candida lipolytica*, *Saccharomyces cerevisiae*, etc.), Plectomycetes (e.g. *Aspergillus clavatus*, *A. niger*, *Penicillium chrysogenum*, *P. rubturm*, etc.), and Pyrenomycetes (e.g. *Chaetomium globosum*, *Sordaria himicola*, etc.).

| Molecules tested | Strains whose growth was inhibited or diminished (%) | Strains whose growth was inhibited by an MIC <10 mg/ml (%) |
|---|---|---|
| Rosmarinic acid | 100 | 96 |
| Oraposide | 92 | 64 |
| Caffeic acid | 83 | 52 |
| Chlorogenic acid | 80 | 40 |
| Verbascoside | 72 | 44 |

EXAMPLE 5

Test for the Inhibition of Aldose Reductase (EC1.1.1.21) (=A.R)

Procedure

Enzyme inhibition was evaluated in vitro using a crude enzyme extract isolated from lenses freshly obtained from bovines and rats. The principle of the reaction is as follows:

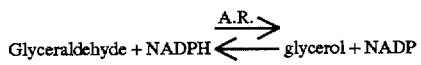

Glyceraldehyde + NADPH ⇌ glycerol + NADP

This reaction takes place at PH=6.2 at ambient temperature and extinctions were measured at 340 nm. The molecules tested were dissolved in twice-distilled water.

The results obtained through the determination of glycerol are expressed as the IC 50 (concentration inhibiting 50% of enzyme activity).

Results

The results are collected in the following table:

| Molecules tested | | IC 50 (mol × L$^{-1}$) |
|---|---|---|
| A.R. calf lens | | |
| Oraposide | (1) | $1.5 \times 10^{-7}$ |
| | (2) | $1.65 \times 10^{-7}$ |
| Verbascoside | (1) | $1.6 \times 10^{-6}$ |
| | (2) | $1.6 \times 10^{-6}$ |
| Arenarioside | (1) | $2.38 \times 10^{-6}$ |
| | (2) | $1.47 \times 10^{-6}$ |
| A.R. - Rat lens | | |
| Oraposide | | $2.20 \times 10^{-7}$ |
| Verbascoside | | $1.78 \times 10^{-6}$ |
| Arenarioside | | $4.18 \times 10^{-6}$ |

The aldose reductase inhibiting activity of the various heteroside caffeic esters (1) and (2) correspond to two different series of experiments.

Conclusion

The four molecules inhibit aldose reductase from both cattle and rats. The most active molecule is oraposide with an IC 50 of $1.6 \times 10^{-7}$ mol/l. It seems to be more active than one of the most promising molecules currently on the market, namely Sorbinil®, which is a synthetic molecule having the formula 6-fluorospirochromane-4,4'-imidazoline-2',5'-dione, for which the IC 50 is $5 \times 10^{-7}$ mol/l.

EXAMPLE 6

Detection of the Anti-Free-Radical Activity of Oraposide in Keratinocyte Cultures Introduction The anti-free-radical activity of oraposide was investigated on a line of human keratinocytes in culture, in comparison with well known anti-free-radical agents.

The protective activity of the anti-free-radical agent was evaluated by measuring malonaldehyde (MDA) in the culture medium (reflecting the lipoperoxidation of cell membrane lipids) after the cells had been brought into contact with a source of oxygenated free radicals (after the method of Z. A. Placer et al., 1966, Anal. Biochem. 16, 359–64, reference cited above).

The cytotoxicity of the substances was also measured by determining lactate dehydrogenase (LDH) at a high concentration (Z.Klin Chem. 1970 8, 658 and Klin. Biochem. 1972, 10, 182).

On the basis of all these results the molecules were classified on the basis of both their anti-free-radical activity and their cytotoxic potential at cell level.

Materials and Methods

Materials:

Cells: human keratinocytes from a squamous carcinoma.

Culture medium: DMEM (½), HAM F12 (½) basic medium (from the Gibco company), with added 5% foetal calf serum (from the Intermed company).

Methods:

Cell Culture and Treatment

Cultures were prepared in 60 mm petri dishes (NUNC), seeding density: 5000 cells per cm².

One week after seeding the merged single layer of cells was processed with 500 1 of a solution containing an oxygenated radical generator consisting of vitamin C $10^{-3}$M, $FeCl_3$ $10^{-4}$M, $FeSO_4$ $10^{-4}$M in pH 8 PBS buffer to which the molecule being tested was added (=reaction medium).

After incubation at 37° C. for 2 hours this incubation medium was recovered for the determination of MDA.

Measurement of LDH

The compounds were tested in solution in DMSO at 200 µM, the control cultures containing an identical amount of solvent.

The amount of LDH released into the culture medium after daily treatment with anti-free-radical molecules was determined after 24 hours and then for 6 days.

The supernatant from the culture was contacted with sodium pyruvate and NADH, and the kinetics of LDH activity were measured spectrophotometrically (Boehringer kit).

LDH activity is revealed by an increase in the OD/min (OD=optical density), which thus reflects the cytotoxicity of the molecule.

Measurement of MDA

After 2 hours incubation with the cells the 500 µl of reaction medium was sampled and thiobarbituric acid was added in order to determine MDA at 532 nm.

The results are stated as % inhibition of MDA production.

Substances Tested

| α tocopherol | } reference substances |
|---|---|
| BHT | |
| Oraposide | |

Results and Discussion

Cytotoxicity

This was tested at 200 µM for the 3 materials. The results are provided for the 1st three days of contact and stated as % increase in OD with respect to the control (+DMSO).

|           | D1       | D2       | D3     |
|-----------|----------|----------|--------|
| α Tocopherol | 19 ± 2  | 83 ± 20  | 54 ± 8 |
| BHT       | 800 ± 80 | 111 ± 15 | —      |
| Oraposide | 0        | 0        | 0      |

(Mean of 3 measurements)

The high cytotoxicity of BHT, which was responsible for an extensive release of LDH from the first day, will be noted. This is less pronounced in the case of α-Tocopherol, whereas oraposide shows no cytotoxic effect upon the cells.

Determination of MDA

The investigation was performed at a concentration of 100 µM for the 3 materials after 2 hours incubation with the reaction mixture. The MDA produced, determined by spectrophotometry, provided results which are expressed as % inhibition of this production in comparison with the controls (reaction medium alone).

The protective power of the anti-radical substance was evaluated from this.

αtocopheral:100%

BHT: 64±2%

Oraposide (1st experiment):70±3%

(2nd experiment): 60±15%

(mean of 3 measurements)

It will be noted that the protective power of oraposide is similar to that of BHT, and a little less powerful than that of α-tocopherol.

Conclusion

Determination of MDA in the culture supernatant made it possible for us to evaluate the anti-free-radical activity of oraposide in a concentration of 100 µM. It proved to be equally effective as BHT, but less effective than α-tocopherol.

However, it should be noted that, unlike these 2 reference molecules, it has no cytotoxic effect up to a concentration of 200 µM.

Various examples of cosmetic or pharmaceutical formulations containing oraposide and these derivatives according to the invention are provided below.

Percentages are given by weight unless indicated otherwise.

EXAMPLE 7

After-Sun Gel (Anti-Inflammatory)

| crude broomrape extract | 20% |
|---|---|
| (in accordance with example 1) | |
| Carbopol 940 ® gel containing 2.5% glycerine | 70% |
| hyaluronic acid | 0.1% |
| conventional preservative | 0.2% |
| perfume | 0.2% |
| H₂O to make up to | 100% |

EXAMPLE 8

Anti-Aging Cream

| Oraposide encapsulated in liposomes (*) | 25% |
|---|---|
| Wheat germ oil | 10% |
| Self-emulsionable base | 5% |
| Water, containing conventional preservatives, perfumes, antioxidants, to make up to | 100% |

(*) The composition of the liposomes containing oraposide is:

| soya lecithin | 3.6 |
|---|---|
| β-sitosterol | 0.4 |
| oraposide | 0.4 |
| soya peptide | 1.0 |
| water to make up to 100%. | |

The oraposide is in the aqueous phase.

EXAMPLE 9

Mark-Lightening Serum

| purified broomrape extract | 5% |
|---|---|
| (as in example 1) | |
| ethanol | 20% |
| glycerinated water | 60% |
| gelling substances | 0.6% |
| perfume | 0.1% |
| preservatives | 0.2% |
| water to make up to | 100% |

EXAMPLE 10

Sun Protectors

| purified broomrape extract | 10% |
|---|---|
| (as in example 1) | |
| micronised titanium | 2% |
| non-ionic emulsifiers | 5% |
| oils | 30% |
| Carbopol 940 ® neutralised gel containing 2.5% | 0.2% |
| silicone | 5% |
| water containing preservatives, antioxidants, perfumes, to make up to | 100% |

EXAMPLE 11

Pharmaceutical Composition

Capsules intended for oral administration containing 60 mg of oraposide or its derivatives of formula I mentioned above are prepared in a conventional excipient for capsules.

These capsules may be used in particular for the treatment of Parkinson's disease in a dose of 4 to 6 capsules per day, which in general is equivalent to 1 to 6 mg of pure oraposide per kg of body weight per day.

The invention also relates to a method for preparing a cosmetic or pharmaceutical composition, and in particular a dermatological composition, characterised in that it comprises the incorporation of an effective amount of oraposide or its aforesaid derivatives in a cosmetically or pharmaceutically acceptable excipient, base or vehicle. Preferably between 0.001% and approximately 10% by weight, and even better between 0.1 and 5% by weight, of oraposide or its derivatives are incorporated in the said composition, in particular in the context of topical application.

The invention also relates to a method for treating conditions caused by free radicals of any origin, characterised in that it comprises the administration of an effective amount of oraposide or its derivatives of formula I aforesaid to a patient suffering from one of the said conditions, in an appropriate form.

In accordance with one embodiment of this treatment process, in particular within the context of topical application, a composition containing 0.001 to 10% by weight, preferably 0.01 to 5% by weight, of oraposide or its aforesaid derivatives is administered.

In accordance with a particular embodiment, inflammations, in particular inflammations caused by excessive exposure to the sun, are treated by the local application, or oral or rectal administration or injection of an effective amount of oraposide or one of its derivatives of formula I aforesaid in order to achieve the desired effect.

In accordance with another variant, cell aging, in particular aging of the skin, and in particular radiation-induced aging, is prevented or treated by the topical application of an effective amount of oraposide or one of its derivatives of formula I aforesaid to achieve the desired effect.

In accordance with another variant, skin is protected against ultraviolet UVA and UVB radiation by the topical application of an effective amount of oraposide or one of its derivatives of formula I aforesaid to obtain the desired ultraviolet protection effect.

In accordance with yet another variant, pigmented skin patches are prevented or treated by the topical application of an effective amount of oraposide or one of its derivatives of formula I aforesaid.

In accordance with yet another embodiment, liver intoxication of any origin is treated by the administration, preferably by oral means or by injection, of an amount of oraposide or one of its derivatives of formula I aforesaid which is effective to achieve the desired effect.

In accordance with yet another embodiment, diabetes, in particular diabetes mellitus, or the lens disturbances which are associated with it, are treated by administering an effective amount of oraposide or one of its derivatives of formula I aforesaid to the patient suffering from the said condition, in an appropriate form.

In accordance with yet another embodiment, pain is treated by administering an effective amount of oraposide or one of its derivatives of formula I aforesaid to the patient suffering from the said pain, in an appropriate form.

In accordance with yet another embodiment, antiallergic treatment is applied by administering an effective amount of oraposide or one of its derivatives of formula I aforesaid to the patient suffering from an allergy, in an appropriate form.

In yet another embodiment, Parkinson's disease is treated by administering an effective amount of oraposide and its derivatives of formula I aforesaid, preferably in combination with L-dopa, to a patient suffering from this disease, in an appropriate form.

In accordance with yet another embodiment, antihypertensive treatment is provided by administering an effective amount of oraposide or one of its derivatives of formula I aforesaid to a patient suffering from arterial hypertension, in an appropriate form.

In accordance with yet another embodiment, anti-tremor treatment is applied by administering an effective amount of oraposide and one of its derivatives of formula I aforesaid to a patient suffering from tremor, in particular tremor due to Parkinson's disease, in an appropriate form.

In accordance with yet another embodiment, an effective amount of oraposide or one of its derivatives of formula I aforesaid sufficient to achieve a psychotropic effect is administered to a patient in an appropriate form.

We claim:

1. A method for treating a patient in need of a treatment selected from the group consisting of scavenging free radicals and protecting from exposure to UV radiation, comprising administering to said patient an effective amount of a compound of formula (I) below:

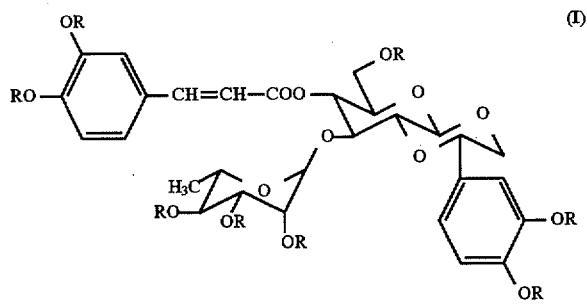

where R is selected from the group consisting of a hydrogen atom, a lower $C_1$–$C_5$ alkyl group, and a $C_1$–$C_6$ acyl group.

2. The method of claim 1, comprising administering a composition containing 0.001 to 10% by weight of oraposide or another compound of formula (I).

3. The method of claim 1, comprising administering a composition containing from 0.01 to 5% by weight of oraposide or another compound of formula (I).

4. The method of claim 1, wherein the patient suffers from inflammation caused by said free radicals.

5. The method of claim 1, comprising the topical application of an effective amount of oraposide or another compound of formula (I), wherein the patient suffers from a condition caused by free radicals selected from the group consisting of cell aging, skin aging, and radiation-induced aging.

6. The method of claim 1, for the treatment of diabetes mellitus caused by free radicals, comprising treating a patient suffering from said condition with an effective amount of oraposide or another compound of formula (I).

7. A method of treatment for pigmented skin patches caused by free radicals comprising topically administering to a patient in need thereof an effective amount of oraposide or its derivatives of formula (I) below:

(I)

where R is selected independently from the group consisting of a hydrogen atom, a lower $C_1$–$C_5$ alkyl group, and a $C_1$–$C_6$ acyl group.

8. The method of claim 1, comprising administering orally or by injection an effective amount of oraposide or another compound of formula (I) wherein the patient suffers from liver intoxication caused by free radicals.

9. A compound of formula (I) below:

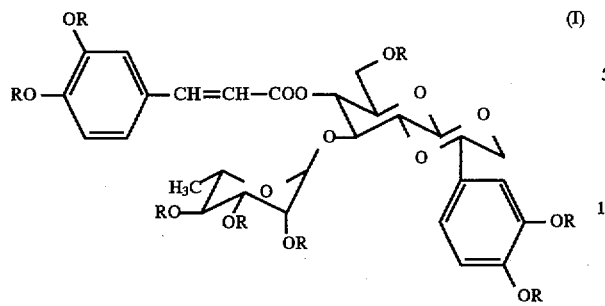

where R is selected from the group consisting of a hydrogen atom, a lower $C_1$–$C_5$ alkyl group, and a $C_1$–$C_6$ acyl group;
provided that, when R is a hydrogen atom, then the compound is in purified form.

10. The compound of claim 9, wherein said alkyl group is methyl.

11. The compound of claim 9, wherein said acyl group is acetyl.

12. The compound of claim 9, wherein only the OR groups on a ring selected from the group consisting of glucopyranosyl and rhamnopyranozyl are acylated.

13. The compound of claim 12, wherein said OR groups are acetylated.

14. The compound of claim 9, wherein only the OR groups on the benzene rings are alkylated.

15. The compound of claim 14 wherein the OR groups on the benzene rings are methylated.

16. The compound of claim 9 wherein said oraposide and its derivatives are extracted from a plant of the family of Orobanchacae.

17. The compound of claim 16 wherein said plant is *Rapum genistae*.

18. A cosmetic or pharmaceutical composition, comprising as an active ingredient an effective amount of a compound of formula (I) below:

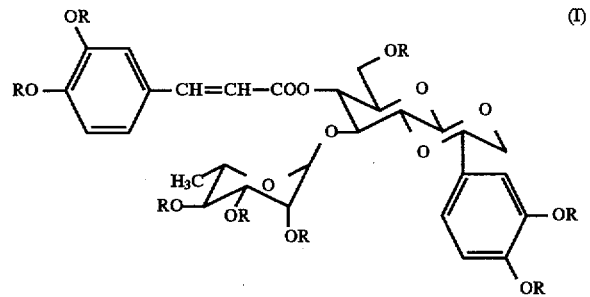

where R is selected independently from the group consisting of a hydrogen atom, a lower $C_1$–$C_5$ alkyl group, and a $C_1$–$C_6$ acyl group; and a cosmetically acceptable or pharmaceutically acceptable carrier therefor;
provided that, when R is a hydrogen atom, then the compound is in purified form.

19. The composition of claim 18 comprising from 0.001 to 10% by weight of said active ingredient.

20. The composition of claim 18 comprising from 0.1 to 5% by weight of said active ingredient.

21. A method for protecting skin against ultraviolet UVA and UVB radiation comprising topically administering to a patient in need thereof an effective amount of oraposide or a compound of formula (I) below:

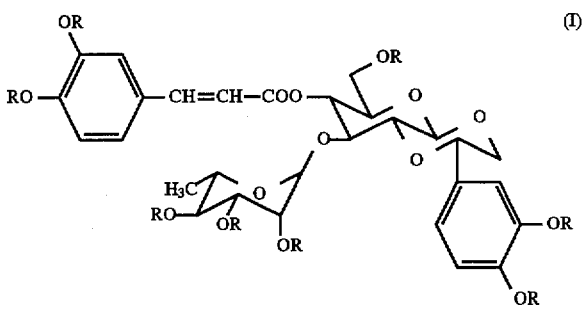

where R is selected independently from the group consisting of a hydrogen atom, a lower $C_1$–$C_5$ alkyl group, and a $C_1$–$C_6$ acyl group.

22. A method for treating a patient suffering from a condition caused by a diabetes mellitus-associated disturbance caused by aldose-reductase comprising administering to said patient an effective amount of oraposide or its derivatives of formula (I) below:

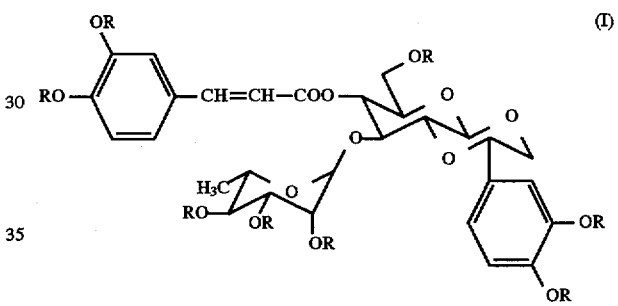

where R is selected independently from the group consisting of a hydrogen atom, a lower $C_1$–$C_5$ alkyl group, and a $C_1$–$C_6$ acyl group.

23. The method as claimed in claim 22, wherein the diabetes mellitus-associated disturbance is a lens disturbance.

24. The method as claimed in claim 1, wherein the compound of formula (I) is in the form of (i) a purified broomrape extract containing at least 30% by weight of oraposide or (ii) a compound of formula (I) other than oraposide obtained by chemical synthesis from oraposide of the purified broomrape extract (i).

25. The composition as claimed in claim 18, wherein the compound of formula (I) is in the form of (i) a purified broomrape extract containing at least 30% by weight of oraposide or (ii) a compound of formula (I) other than oraposide obtained by chemical synthesis from oraposide of the purified broomrape extract (i).

26. The method of claim 5, wherein skin aging is radiation-induced aging.

* * * * *